(12) United States Patent
Rotella et al.

(10) Patent No.: US 9,968,350 B2
(45) Date of Patent: May 15, 2018

(54) BLUNTED SAFETY NEEDLE

(71) Applicant: Avent, Inc., Alpharetta, GA (US)

(72) Inventors: John Anthony Rotella, La Jolla, CA (US); Nathan Christopher Griffith, Johns Creek, GA (US); Lanita Grayce Cox, Suwanee, GA (US); Donald Jay McMichael, Roswell, GA (US)

(73) Assignee: Avent, Inc., Alpharetta, GA (US)

( * ) Notice: Subject to any disclaimer, the term of this patent is extended or adjusted under 35 U.S.C. 154(b) by 0 days. days.

(21) Appl. No.: 15/000,625

(22) Filed: Jan. 19, 2016

(65) Prior Publication Data

US 2016/0128686 A1 May 12, 2016

Related U.S. Application Data

(63) Continuation of application No. 11/848,523, filed on Aug. 31, 2007, now abandoned.

(51) Int. Cl.
| | | |
|---|---|---|
| *A61B 17/04* | (2006.01) | |
| *A61M 5/32* | (2006.01) | |
| *A61B 17/34* | (2006.01) | |
| *A61B 90/00* | (2016.01) | |
| *A61B 17/00* | (2006.01) | |

(52) U.S. Cl.
CPC ...... *A61B 17/0401* (2013.01); *A61B 17/3496* (2013.01); *A61M 5/32* (2013.01); *A61B 2017/00477* (2013.01); *A61B 2017/0409* (2013.01); *A61B 2017/0417* (2013.01); *A61B 2090/034* (2016.02); *A61B 2090/037* (2016.02); *A61B 2090/0801* (2016.02); *A61M 2005/3212* (2013.01)

(58) Field of Classification Search
CPC ...... A61M 25/0643; A61M 2005/3212; A61M 5/321; A61M 25/0612; A61M 5/1626; A61M 5/3243
See application file for complete search history.

(56) References Cited

U.S. PATENT DOCUMENTS

| | | |
|---|---|---|
| 2,075,508 A | 1/1937 | Davison |
| 3,438,373 A | 4/1969 | Pannier, Jr. |
| 3,664,345 A | 5/1972 | Dabbs et al. |
| 4,249,535 A | 2/1981 | Hargest, III |

(Continued)

FOREIGN PATENT DOCUMENTS

| | | |
|---|---|---|
| EP | 1 110 576 A1 | 6/2001 |
| EP | 1 159 919 A2 | 12/2001 |

(Continued)

OTHER PUBLICATIONS

Patent Cooperation Treaty Search Report from the International Search Application No. PCT/IB2008/052421, dated Dec. 5, 2008.

*Primary Examiner* — Kami A Bosworth
*Assistant Examiner* — William Carpenter
(74) *Attorney, Agent, or Firm* — Dority & Manning, P.A.

(57) ABSTRACT

A blunted safety needle is provided, which includes a hollow needle having a sharp distal tip and a stylus having a blunted end. The stylus is positioned within at least a portion of the needle. After the needle is used to deliver or deploy a substance and/or a device, the blunted end of the stylus is positioned to extend through the sharp distal tip of the needle and un-releaseably lock into position, thereby providing a blunted safety needle assembly.

14 Claims, 10 Drawing Sheets

(56) References Cited

U.S. PATENT DOCUMENTS

| | | | |
|---|---|---|---|
| 4,291,698 A | 9/1981 | Fuchs et al. | |
| 4,315,513 A | 2/1982 | Nawash et al. | |
| 4,393,873 A | 7/1983 | Nawash et al. | |
| 4,627,841 A | 12/1986 | Dorr | |
| 4,666,433 A | 5/1987 | Parks | |
| 4,669,473 A * | 6/1987 | Richards | A61B 17/0401 606/215 |
| 4,685,901 A | 8/1987 | Parks | |
| 4,701,163 A | 10/1987 | Parks | |
| 4,705,040 A | 11/1987 | Mueller et al. | |
| 4,798,592 A | 1/1989 | Parks | |
| 4,823,794 A | 4/1989 | Pierce | |
| 4,852,568 A | 8/1989 | Kensey | |
| 4,890,612 A | 1/1990 | Kensey | |
| 5,019,093 A | 5/1991 | Kaplan et al. | |
| 5,037,479 A | 8/1991 | Hermes et al. | |
| 5,041,129 A | 8/1991 | Hayhurst et al. | |
| 5,049,138 A | 9/1991 | Chevalier et al. | |
| 5,051,272 A | 9/1991 | Hermes et al. | |
| 5,053,047 A | 10/1991 | Yoon | |
| 5,061,274 A | 10/1991 | Kensey | |
| 5,074,846 A | 12/1991 | Clegg et al. | |
| 5,112,310 A | 5/1992 | Grobe | |
| 5,121,836 A | 6/1992 | Brown et al. | |
| 5,123,912 A | 6/1992 | Kaplan et al. | |
| 5,123,914 A | 6/1992 | Cope | |
| 5,129,511 A | 7/1992 | Brown et al. | |
| RE34,021 E | 8/1992 | Mueller et al. | |
| 5,154,283 A | 10/1992 | Brown | |
| 5,167,627 A | 12/1992 | Clegg et al. | |
| 5,192,302 A | 3/1993 | Kensey et al. | |
| 5,222,976 A | 6/1993 | Yoon | |
| 5,222,978 A | 6/1993 | Kaplan et al. | |
| 5,226,912 A | 7/1993 | Kaplan et al. | |
| 5,246,104 A | 9/1993 | Brown et al. | |
| 5,258,015 A | 11/1993 | Li et al. | |
| 5,261,210 A | 11/1993 | Brown | |
| 5,261,886 A | 11/1993 | Chesterfield et al. | |
| 5,269,809 A | 12/1993 | Hayhurst et al. | |
| 5,273,529 A | 12/1993 | Idowu | |
| 5,306,289 A | 4/1994 | Kaplan et al. | |
| 5,307,924 A | 5/1994 | Manosalva et al. | |
| 5,312,345 A * | 5/1994 | Cole | A61M 25/0643 604/110 |
| 5,312,435 A | 5/1994 | Nash et al. | |
| 5,316,013 A | 5/1994 | Striebel et al. | |
| 5,318,543 A | 6/1994 | Ross et al. | |
| 5,330,503 A | 7/1994 | Yoon | |
| 5,341,823 A | 8/1994 | Manosalva et al. | |
| 5,359,831 A | 11/1994 | Brown et al. | |
| 5,366,081 A | 11/1994 | Kaplan et al. | |
| RE34,866 E | 2/1995 | Kensey et al. | |
| 5,388,589 A * | 2/1995 | Davis | A61B 10/0275 600/562 |
| 5,391,159 A | 2/1995 | Hirsch et al. | |
| 5,417,036 A | 5/1995 | Brown | |
| 5,425,445 A | 6/1995 | Brown et al. | |
| 5,447,966 A | 9/1995 | Hermes et al. | |
| 5,451,212 A | 9/1995 | Andersen | |
| 5,456,697 A | 10/1995 | Chesterfield et al. | |
| 5,462,162 A | 10/1995 | Kaplan et al. | |
| 5,468,252 A | 11/1995 | Kaplan et al. | |
| 5,531,699 A | 7/1996 | Tomba et al. | |
| 5,531,759 A | 7/1996 | Kensey et al. | |
| 5,531,761 A | 7/1996 | Yoon | |
| 5,545,178 A | 8/1996 | Kensey et al. | |
| 5,626,614 A | 5/1997 | Hart | |
| 5,702,352 A | 12/1997 | Kimura et al. | |
| 5,743,882 A | 4/1998 | Luther | |
| 5,851,195 A | 12/1998 | Gill | |
| 6,030,364 A | 2/2000 | Durgin et al. | |
| 6,039,714 A | 3/2000 | Cracauer et al. | |
| 6,063,106 A | 5/2000 | Gibson | |
| 6,077,250 A | 6/2000 | Snow et al. | |
| 6,090,073 A | 7/2000 | Gill | |
| 6,106,499 A | 8/2000 | Overton et al. | |
| 6,110,183 A | 8/2000 | Cope | |
| 6,186,985 B1 | 2/2001 | Snow | |
| 6,260,699 B1 | 7/2001 | Kaplan et al. | |
| 6,270,480 B1 | 8/2001 | Dorr et al. | |
| 6,293,961 B2 | 9/2001 | Schwartz et al. | |
| 6,315,789 B1 | 11/2001 | Cragg | |
| 6,319,271 B1 | 11/2001 | Schwartz et al. | |
| 6,328,720 B1 | 12/2001 | McNally et al. | |
| 6,332,877 B1 | 12/2001 | Michels | |
| 6,402,722 B1 | 6/2002 | Snow et al. | |
| 6,432,123 B2 | 8/2002 | Schwartz et al. | |
| 6,450,937 B1 | 9/2002 | Mercereau et al. | |
| 6,475,189 B1 | 11/2002 | Lilley, Jr. | |
| 6,544,239 B2 | 4/2003 | Kinsey et al. | |
| 6,582,443 B2 | 6/2003 | Cabak | |
| 6,626,919 B1 | 9/2003 | Swanstrom | |
| 6,629,956 B1 | 10/2003 | Polidoro et al. | |
| 6,629,957 B1 * | 10/2003 | Wiklund | A61M 5/3243 604/192 |
| 6,669,707 B1 | 12/2003 | Swanstrom et al. | |
| 6,673,058 B2 | 1/2004 | Snow | |
| 6,699,263 B2 | 3/2004 | Cope | |
| 6,773,440 B2 | 8/2004 | Gannoe et al. | |
| 6,837,872 B2 * | 1/2005 | Crawford | A61M 5/32 600/576 |
| 6,896,665 B2 | 5/2005 | Picha et al. | |
| 6,902,541 B2 | 6/2005 | McNally et al. | |
| 6,966,916 B2 | 11/2005 | Kumar | |
| 6,997,931 B2 | 2/2006 | Sauer et al. | |
| 7,033,380 B2 | 4/2006 | Schwartz et al. | |
| 7,066,944 B2 | 6/2006 | Laufer et al. | |
| 2003/0040710 A1 | 2/2003 | Polidoro | |
| 2003/0120222 A1 | 6/2003 | Vaillancourt | |
| 2004/0034369 A1 | 2/2004 | Sauer et al. | |
| 2004/0153103 A1 | 8/2004 | Schwartz et al. | |
| 2005/0004540 A1 | 1/2005 | McNally et al. | |
| 2005/0143691 A1 | 6/2005 | Picha et al. | |
| 2005/0149120 A1 | 7/2005 | Collier et al. | |
| 2005/0149121 A1 | 7/2005 | Crombie et al. | |
| 2005/0165419 A1 | 7/2005 | Sauer et al. | |
| 2005/0203550 A1 | 9/2005 | Laufer et al. | |
| 2006/0095008 A1 | 5/2006 | Lampropoulos et al. | |
| 2006/0100643 A1 | 5/2006 | Laufer et al. | |
| 2006/0135996 A1 | 6/2006 | Schwartz et al. | |

FOREIGN PATENT DOCUMENTS

| | | |
|---|---|---|
| EP | 1 749 481 A1 | 2/2007 |
| WO | WO 95/03837 | 2/1995 |
| WO | WO 1998/026821 A1 | 6/1998 |
| WO | WO 02/066108 | 8/2002 |
| WO | WO 2006/111394 | 10/2006 |

\* cited by examiner

BLUNTED SAFETY NEEDLE

RELATED APPLICATION

The present application is a Continuation application of U.S. application Ser. No. 11/848,523, filed Aug. 31, 2007.

BACKGROUND OF THE INVENTION

This invention relates to a hollow needle for use in the percutaneous fixation of a hollow organ, blood vessel, and so forth, in a mammal body, which has an apparatus for rendering it blunted.

Health care providers are at risk of exposure to blood-borne pathogens, including, for example, hepatitis B, hepatitis C, HIV, and the like. The risk of an accidental stick from a sharp object, such as a needle, exists in many medical procedures. One such procedure is gastropexy, in which a needle is used to pierce a patient's abdominal wall to place one or more fasteners in a patient's stomach. Such a needle must be sharp, so that it penetrates through the patent's skin and abdominal wall to the targeted hollow organ. A fastener, such as a "T-bar" fastener, carried at or near the tip of the needle, is desirably deployed by the needle and positioned against an inner wall of the stomach. A tensioning suture is connected to the fastener and, at an opposite end of the suture on the outer surface of the patient's body, the suture is desirably also connected to a suture holder which permits adjustment of the tension on the suture. In this manner, the stomach wall is more closely positioned to the outer surface of the patient's body, and stabilized in this position. Such a procedure is used to isolate a portion of a patient's stomach, so that a tissue opening or stoma may be created to permit placement of a feeding tube, and so forth.

After the fastener has been deployed by the needle, the needle still remains as a sharp hazard, in its position inside of the patient's stomach, as well as when it is removed therefrom. Therefore, there is a need to provide an apparatus which permits blunting of the needle after the fastener is positioned by the needle. Desirably, the needle may be blunted while it is in a position in the patient's stomach. Further, it is desirable that a health care provider easily detect whether the needle has been blunted once a safety apparatus has been activated. Once activated, the blunting safety apparatus desirably may not be deactivated, such that the needle is rendered a sharp hazard again. Finally, such a blunting safety apparatus is desirably activated by a single-handed technique, i.e., the hand holding a proximal end of the needle, thereby allowing the health care provider's hands to remain away from a sharp distal end of the needle during such activation of a safety blunting apparatus.

Definitions

As used herein, the term "stylus" refers to a solid or hollow rod which has a blunted, non-sharp distal end, which is sized to fit and move within and extend through at least a sharp end of a hollow needle. The stylus is desirably, but not by way of limitation, made from the same material as the sharp end of the needle. However, the stylus may be made from any material(s) so long as it operates as shown and/or described herein.

As used herein, the terms "comprise", "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "has" and/or "have", and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

As used herein, the terms "resilient", "resilience" and/or "resiliency" and any derivatives thereof refers to the physical property of an object and/or a material that can return to its original form, shape and/or position after deformation such as being bent, compressed, or stretched that does not exceed its elastic limit.

As used herein, the term "couple" includes, but is not limited to, joining, connecting, fastening, linking, or associating two things integrally or interstitially together.

As used herein, the term "configure" or "configuration", and derivatives thereof means to design, arrange, set up, or shape with a view to specific applications or uses. For example: a military vehicle that was configured for rough terrain; configured the computer by setting the system's parameters.

As used herein, the terms "substantial" or "substantially" refer to something which is done to a great extent or degree; a significant or great amount; for example, as used herein "substantially" as applied to "substantially" covered means that a thing is at least 70% covered.

As used herein, the term "alignment" refers to the spatial property possessed by an arrangement or position of things in a straight line or in parallel lines.

As used herein, the terms "orientation" or "position" used interchangeably herein refer to the spatial property of a place where or way in which something is situated; for example, "the position of the hands on the clock."

As used herein, the term "about" refers to an amount that is plus or minus 10 percent of a stated number or a stated or implied range. These terms may be defined with additional language in the remaining portions of the specification.

SUMMARY OF THE INVENTION

In response to the difficulties and problems discussed herein, a safety needle assembly is provided. It comprises a needle including a shaft having a sharp open distal end and an open proximal end. The proximal end has a needle hub. The needle hub has an opening which is continuous with an opening provided through the shaft of the needle. The needle hub includes at least one movable stop positioned. The safety needle assembly also includes a stylus. The stylus has a shaft which includes a blunt distal end and a proximal end, which has a stylus hub. The hub includes an edge. When the stylus is positioned inside of the needle, the blunt distal end of the stylus extends a distance toward the open distal end of the needle. The stylus is held in a position preventing movement toward the distal end of the needle by a position of the movable stop against the edge. When the movable stop is moved away from the edge of the stylus, the blunt distal end of the stylus is movable to extend through and beyond the sharp open distal end of the needle thereby rendering the safety needle assembly in a blunted condition. The stylus is configured to non-releasably couple to the needle to provide an unmovable position of the stylus with respect to the needle.

In another aspect of the invention, a safety needle assembly is provided. The safety needle assembly comprises a needle including a shaft having a sharp open distal end and an open proximal end. The proximal end has a needle hub. The needle hub has an opening which is continuous with an opening provided through the shaft of the needle. The hub includes at least one recess. The safety needle assembly also includes a stylus. The stylus has a shaft including a blunt distal end and a proximal end having a stylus hub. The hub includes a retainer. The stylus is held in a first position when the stylus is positioned inside of the needle, and the blunt distal end of the stylus extends a distance toward the open distal end of the needle but is retained within the shaft of the needle by a portion of the retainer held in one recess in the needle hub. When the hub of the stylus is pushed to move the blunt distal end of the stylus within the shaft of the needle, the stylus moves within the shaft until the blunt distal end extends beyond the sharp distal end of the needle and the portion of the retainer is positioned in another recess in the needle hub. This position renders the safety needle assembly in a blunted condition. The stylus is configured to non-releasably couple to the needle to provide an unmovable position of the stylus with respect to the needle to maintain the blunted condition.

In yet another aspect of the invention, a safety needle assembly is provided. The safety needle assembly comprises a needle including a shaft having a sharp open distal end and an open proximal end. The proximal end has a needle hub. The needle hub has an opening which is continuous with an opening provided through the shaft of the needle. The needle hub includes at least one movable stop positioned thereon and at least one recess therein. The safety needle assembly also includes a stylus. The stylus has a shaft including a blunt distal end and a proximal end having a stylus hub. The hub has an edge and a retainer. The stylus is held in a first position when the stylus is positioned inside of the needle, the blunt distal end of the stylus extends a distance toward the open distal end of the needle but is retained within the shaft of the needle by a portion of the retainer held in one recess in the needle hub and by a position of the movable stop against the edge of the stylus hub. When the movable stop is moved away from the edge, the blunt distal end of the stylus is movable to extend through and beyond the sharp open distal end of the needle and the portion of the retainer is positioned in another recess in the needle hub, thereby rendering the safety needle assembly in a blunted condition. The stylus is configured to non-releasably couple to the needle to provide an unmovable position of the stylus with respect to the needle to maintain the blunted condition.

Additional features and advantages of the present invention will be revealed in the following detailed description. Both the foregoing summary and the following detailed description and examples are merely representative of the invention, and are intended to provide an overview for understanding the invention as claimed.

DETAILED DESCRIPTION

Reference will now be made in detail to one or more embodiments of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Figure 1:
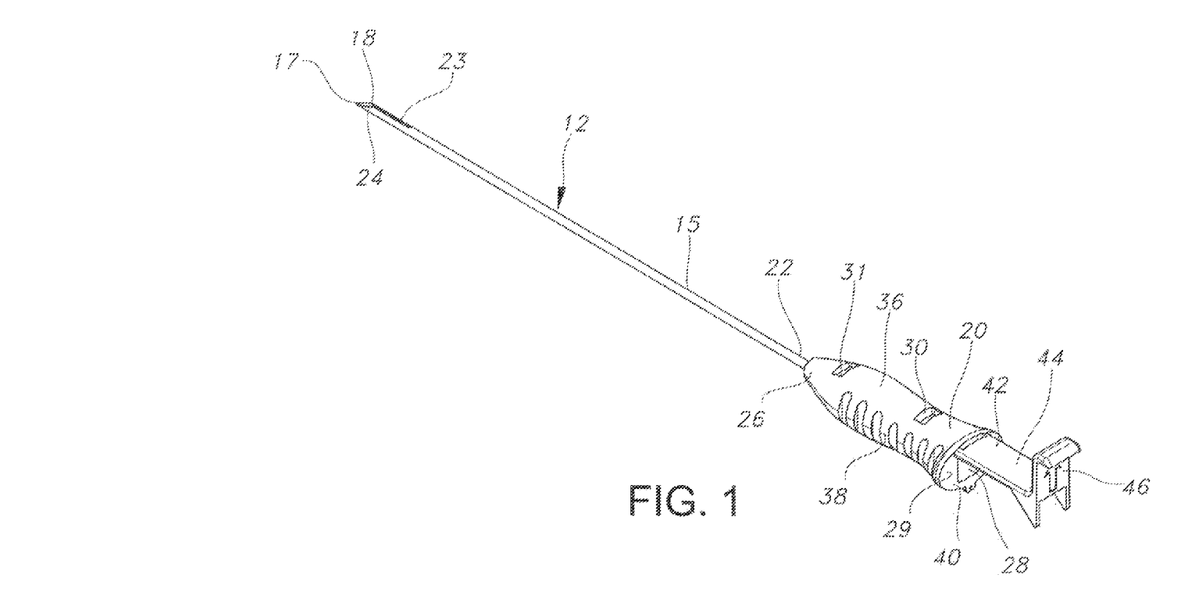
FIG. 1 is a perspective view of a portion of a safety needle assembly of the present invention, showing the needle and its associated hub.
Figure 2:
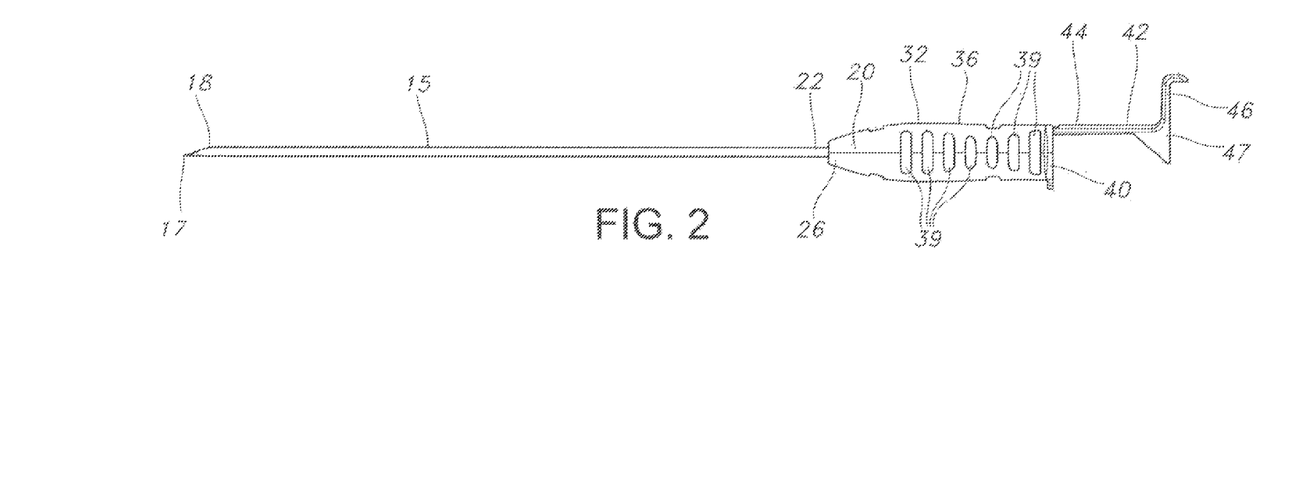
FIG. 2 is side elevational view of the portion of the safety needle assembly of FIG. 1, but showing one surface of the hub with apertures therein.
Figure 3:
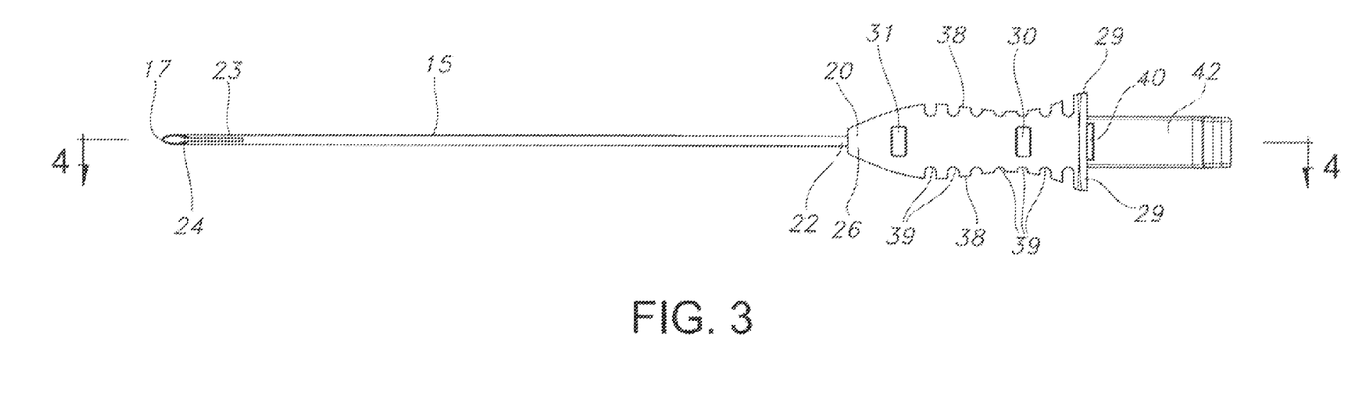
FIG. 3 is a top plan view of the portion of the safety needle assembly of FIG. 1, but showing another surface of the hub with grooves therein.
Figure 4:
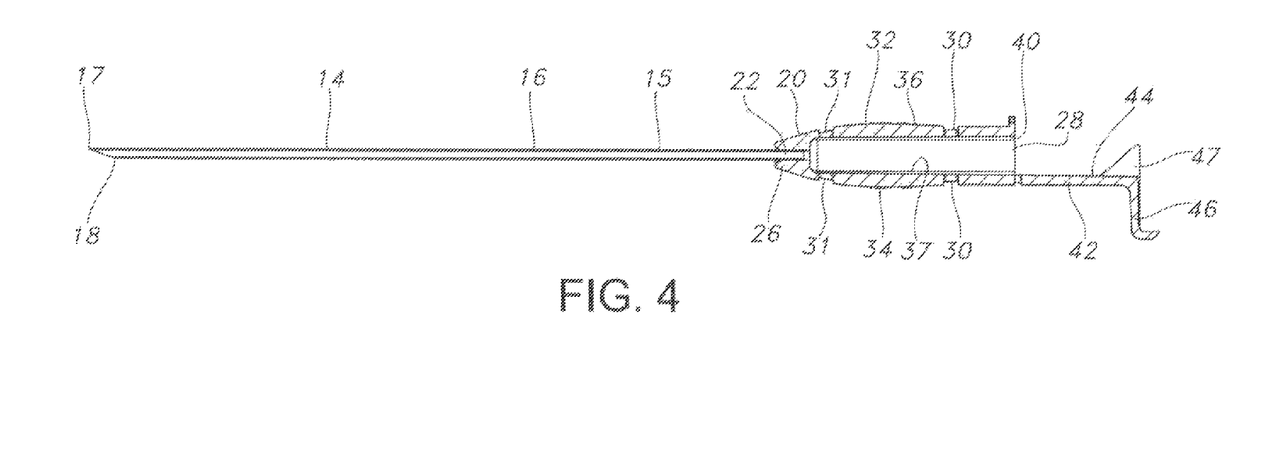
FIG. 4 is a sectional view of FIG. 3, taken at lines 4-4.

A safety needle assembly is rendered safe by positioning a blunt stylus therethrough, which results in blunting of the assembly. Referring now to FIGS. 1-16 in general, and 1-4 in particular, the present invention provides a safety needle assembly 10. The safety needle assembly 10 includes a metal needle 12 having an opening 14 extending through a metal shaft 15, which defines an inner surface 16 (FIG. 4). A tapered sharp tip 17 is positioned at a distal end 18 of the needle 12. A needle hub 20 is coupled at or near a proximal end 22 of the needle 12. A slot 23 may be formed desirably, but not by way of limitation, at a lower edge 24 of the tapered distal tip 16 of the needle 12.

A distal end 26 of the needle hub 20 is coupled about a portion of the proximal end 22 of the needle 12. The needle hub 20 includes an opening 28 that is continuous with the opening 14 that extends through the hollow shaft 15 of the needle 12 and through the distal tip 16 thereof. The needle hub also desirably includes opposing spaced-apart edges 29 at the proximal end 22 thereof. The needle hub 20 desirably has a pair of upper apertures or upper recesses 30, one upper recess 30 positioned on each of the relatively flat sides 32, 34 on an outer surface 36 of the hub 20 near a proximal end 40 thereof. Another pair of lower apertures or lower recesses 31, one lower recess 31 positioned on each of the relatively flat sides 32, 34 on an outer surface 36 of the hub 20 and near the distal end 26 thereof. The apertures or recesses 30, 31 extend from the outer surface 36 to the opening 28 in the needle hub 20. The purpose for the apertures or recesses 30, 31 will be discussed in detail below.

An inner surface 37 (FIG. 4) is provided and is defined by opening 28 formed through the needle hub 20. The inner surface 37 is sized to receive a blunted stylus therethrough. The hub 20 includes a pair of relatively short sides 38 as well, which are spaced-apart from each other, but are adjacent to the flat sides 32, 36. Each short side 38 has a plurality of grooves 39 formed therein to facilitate gripping the hub 20.

The needle hub 20 also includes, at the proximal end 40, a handle 42 which is desirably positioned to extend away from the proximal end 40. The handle 42 may desirably include a handle shaft 44 generally axially aligned with the needle hub 20 and which is desirably integrally formed with the proximal end 40 of the needle hub 20. The handle 42 also desirably includes a handle portion 46 which extends at an angle, desirably at about a 90 degree angle, transversely away from the handle shaft 44. A pair of wedges 47 are positioned in a spaced-apart orientation on either side of a junction of the shaft 44 and the handle portion 46. The wedges 47 are positioned to function as stops, as will be described in further detail below. The needle hub 20 may also include a "C"-clip (not shown) to hold a suture which may be positioned at least partially in the needle 12.

Figures 5, 6:
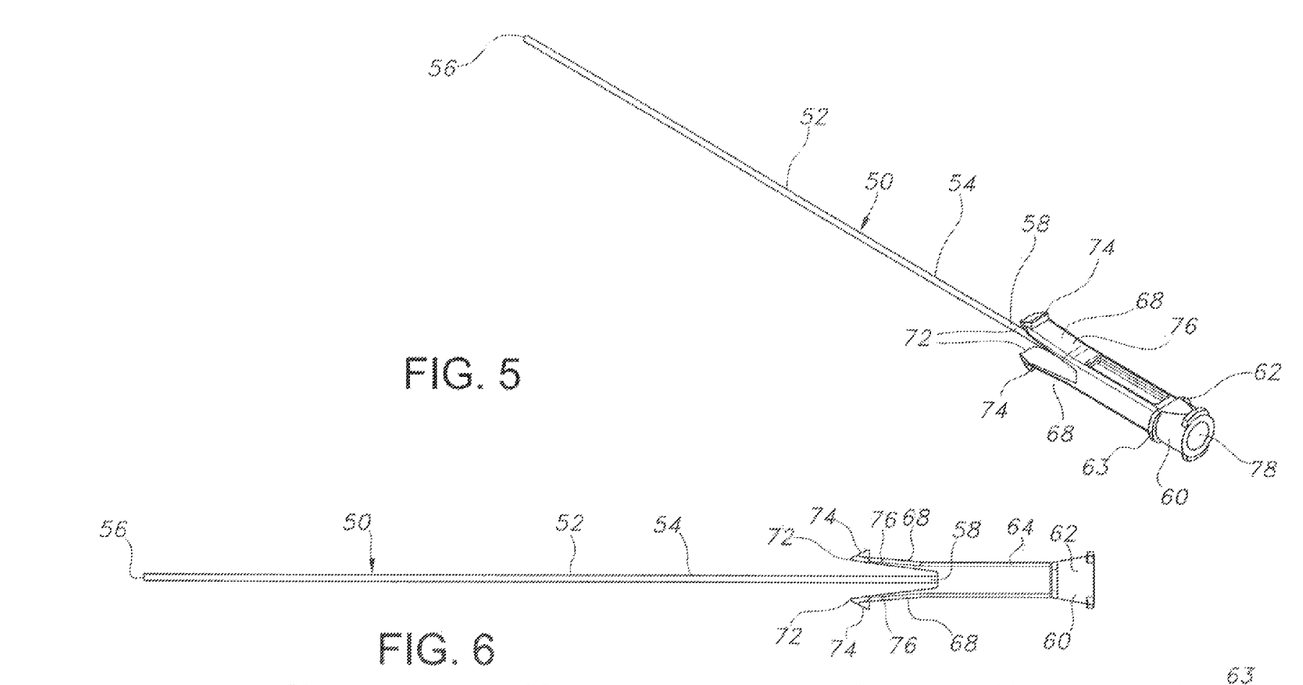
FIG. 5 is a perspective view of another portion of the safety needle assembly of the present invention, showing a stylus and its associated hub.
FIG. 6 is a side elevational view of the stylus and hub of FIG. 5, showing the flanges, each with a clip at a free end thereof.
Figure 7:
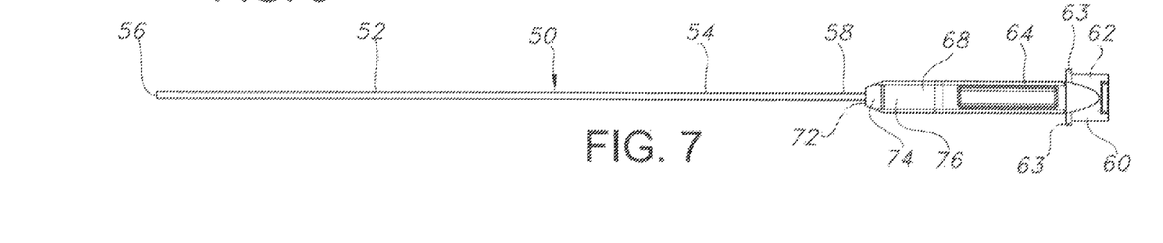
FIG. 7 is a top plan view of the stylus and hub of FIG. 5, showing the flanges with clips.

The blunted safety needle assembly 10 also includes a stylus 50, as illustrated in FIGS. 5-7, having a solid or hollow shaft 52 sized to have an outer surface 54 which cooperates to substantially fill a diameter of the inner surface 28 of the needle 12. The stylus 50 includes a blunted, non-sharp, distal end 56 and a proximal end 58 which is coupled to a stylus hub 60. The distal end 56 is sized and configured to position against and move a fastener positioned near the distal end 18 in the shaft 15 of the needle 12.

Figure 15:
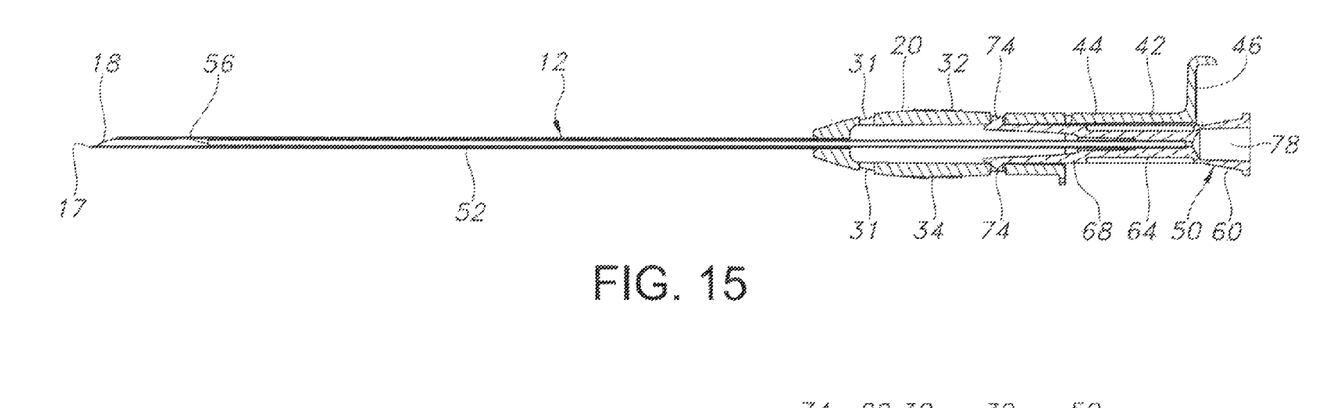
FIG. 15 is a sectional view of FIG. 12, showing the clips of the flanges in the upper apertures of the needle hub.
Figure 16:
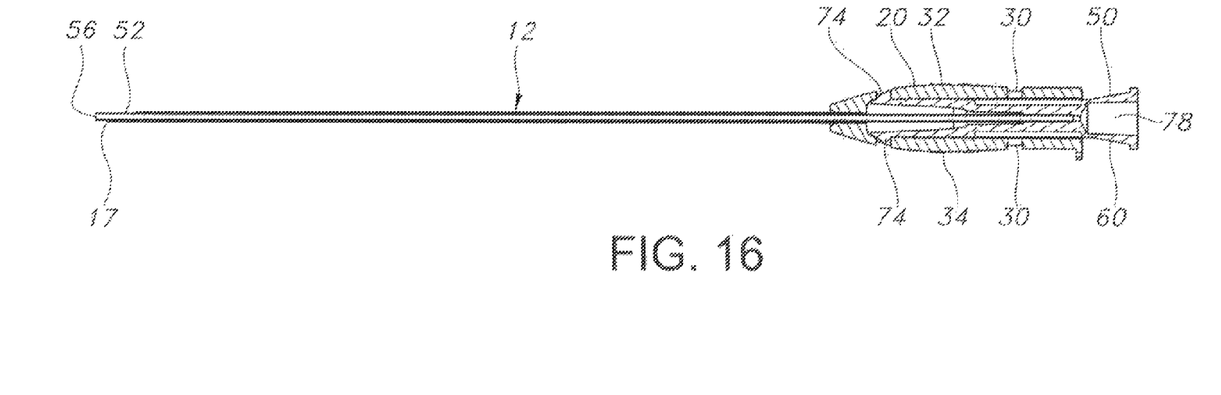
FIG. 16 is a sectional view similar to FIG. 13, showing the clips of the flanges in the lower apertures of the needle hub, and the blunt distal end of the stylus positioned through the distal end of the needle to render the needle assembly in a blunted position.

The stylus hub 60 includes, at one end, a cylindrical upper hub 62 which desirably includes a standard luer lock. At an opposite end of the upper hub 62 is a narrower-diameter lower hub 64 which desirably couples about at least a portion of the proximal end 58 of the stylus 50. A protruding rim or ridge 63 may extends about a circumference of the junction of the upper hub 62 and the lower hub 64. A pair of flanges 68 extend from the lower hub 64 and include free ends 72 which extend away from the upper hub 62 and toward the distal end 56 of the stylus 50, but are in a substantial axial alignment therewith. The flanges 68 flare slightly away from the stylus shaft 52. Generally triangularly-shaped (in a side elevational view) clips 74 (FIG. 6) extend outward on an outer surface 76 of each flange 68 at each free end 72 of the flange 68. The flanges 68 and clips 74 thereon provide a retainer. It will be understood that at least a portion of the stylus hub 60, that is, at least the flanges 68, is sized to extend into and contact the inner surface 37 of the needle hub 20 (FIGS. 15 and 16). The stylus 50 may include an opening 78 through hubs 60, 64 and the shaft 52 of the stylus 50.

Figure 8:
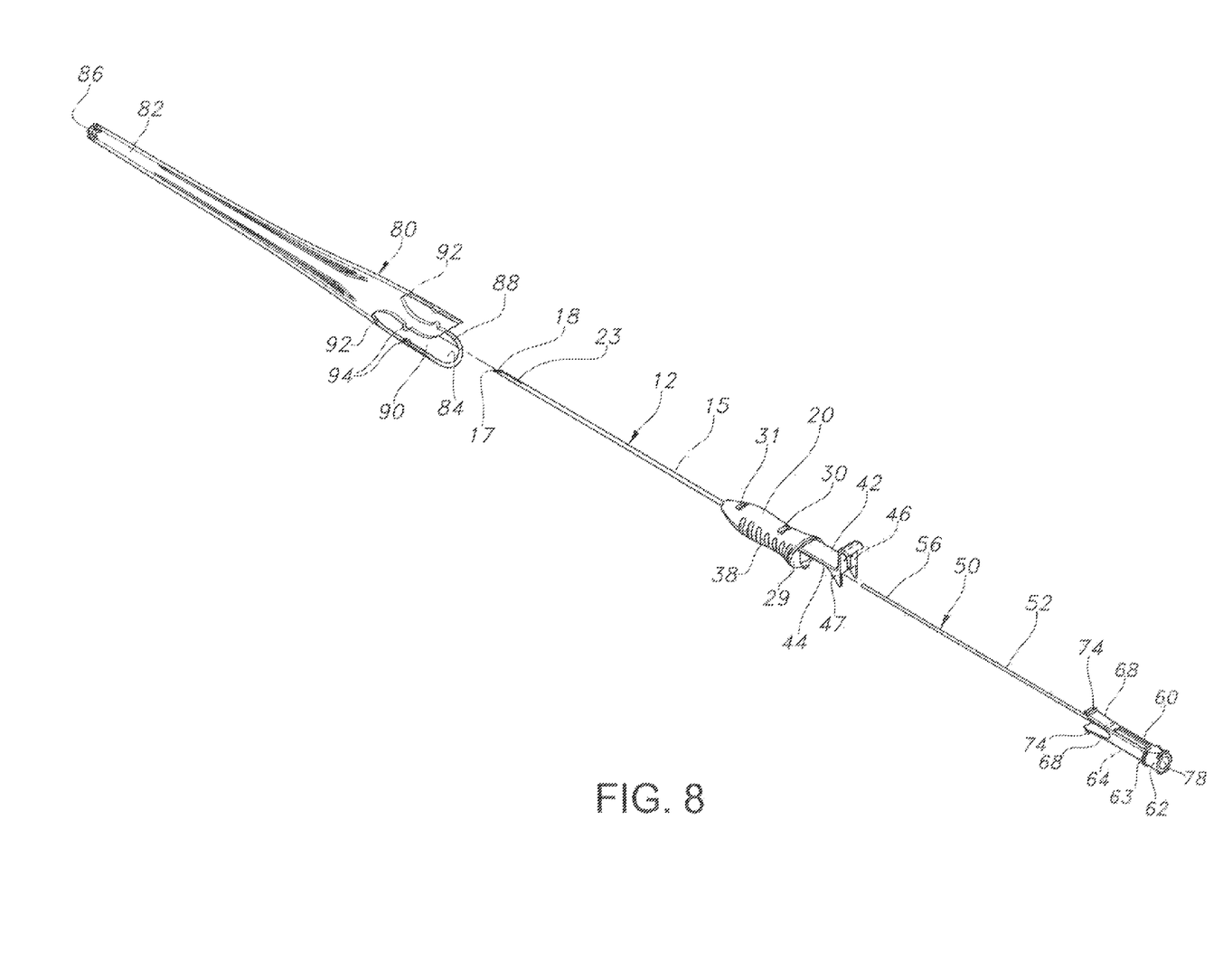
FIG. 8 is an exploded perspective view of the safety needle assembly and including a sheath.
Figure 9:
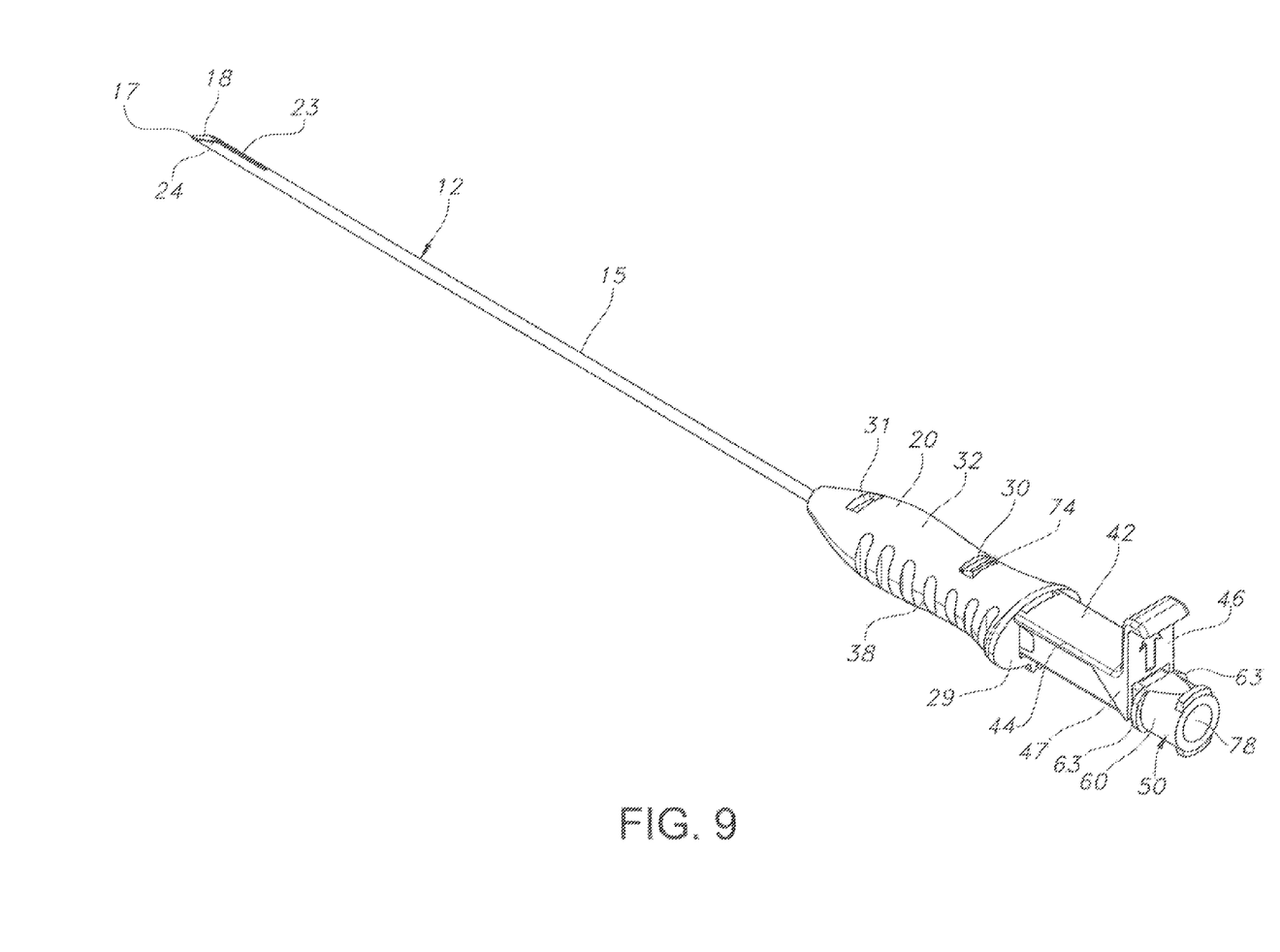
FIG. 9 is a perspective view of the safety needle assembly, showing the stylus positioned in at least a portion of the needle.
Figure 10:
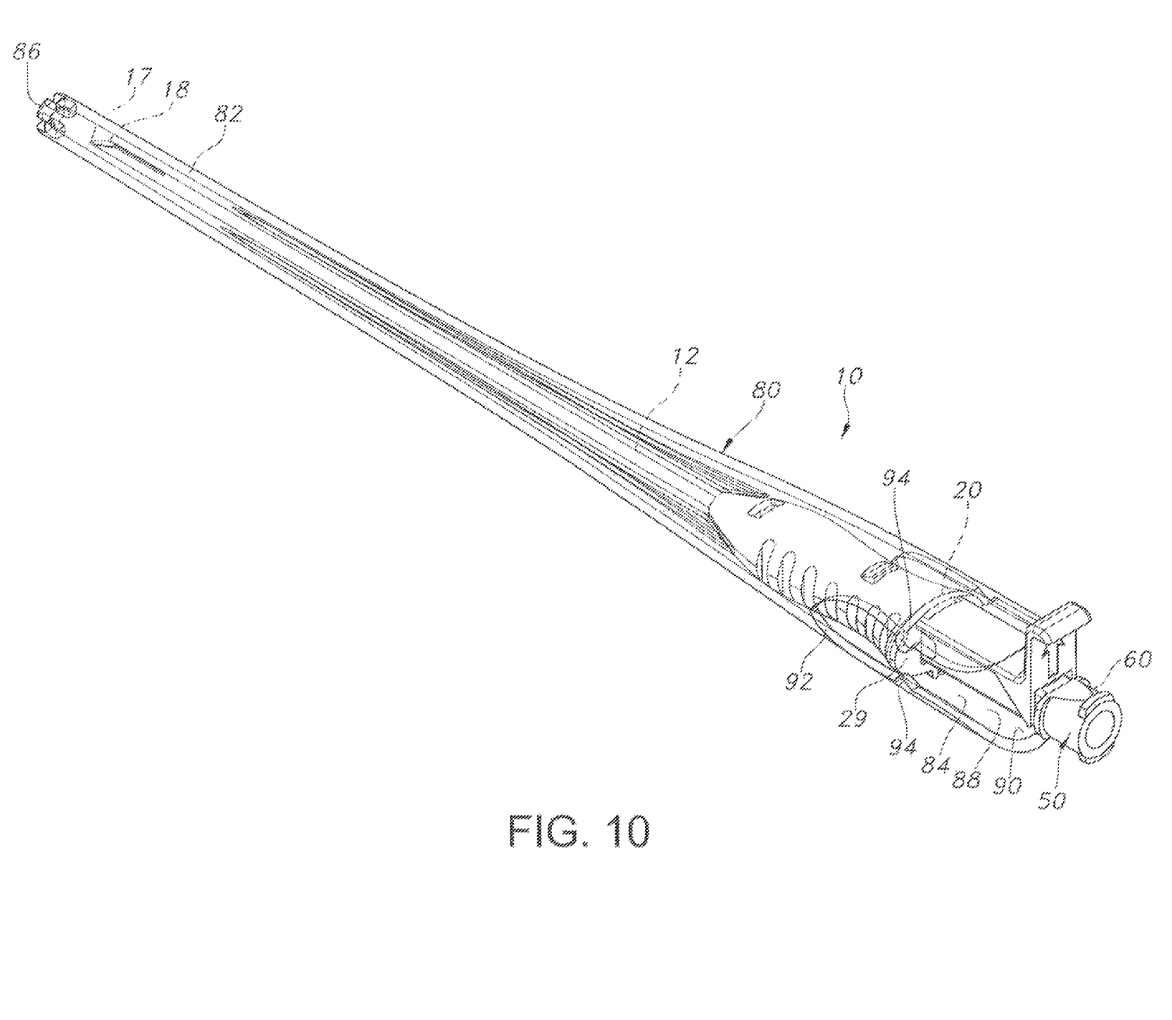
FIG. 10 is a perspective view of the safety needle assembly positioned in the sheath.
Figure 11:
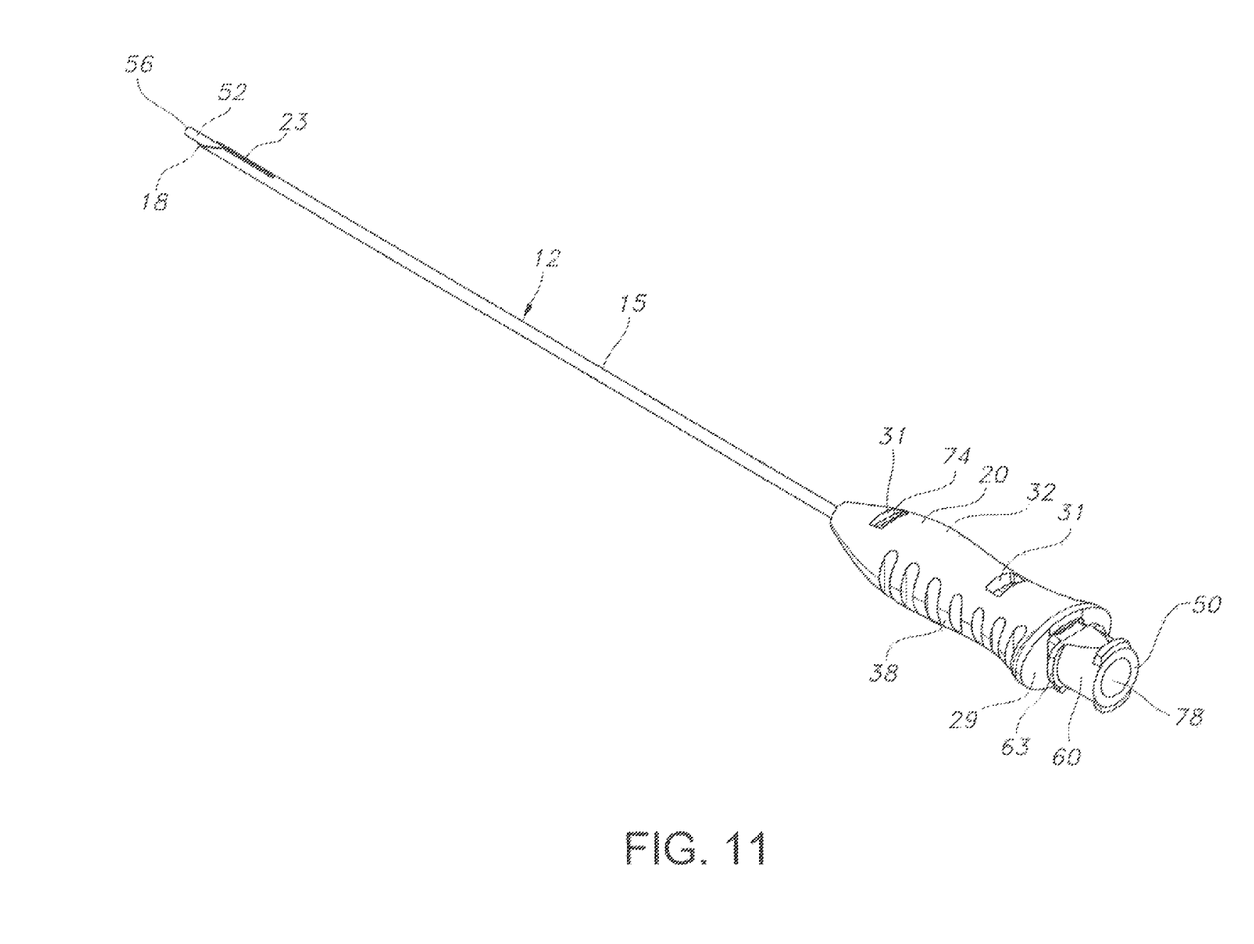
FIG. 11 is a perspective view of the safety needle assembly, showing the stylus extending through the needle, thereby rendering the needle blunt.
Figure 12:
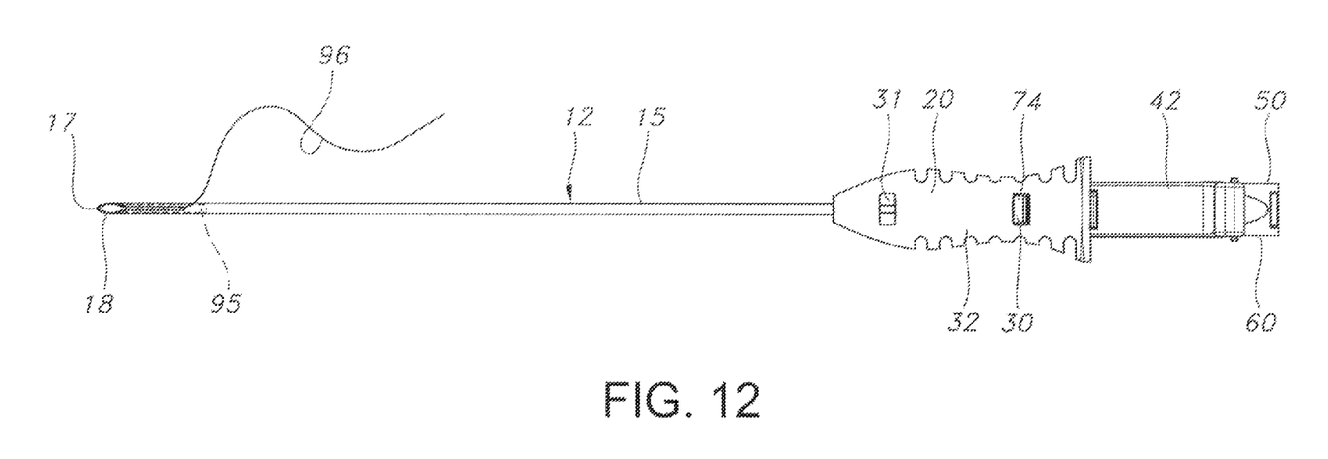
FIG. 12 is a top plan view of the safety needle assembly, showing the stylus in the needle a T-bar fastener positioned therein (shown in phantom lines), a suture extending from the T-bar fastener and through the slit in the needle.
Figure 13:
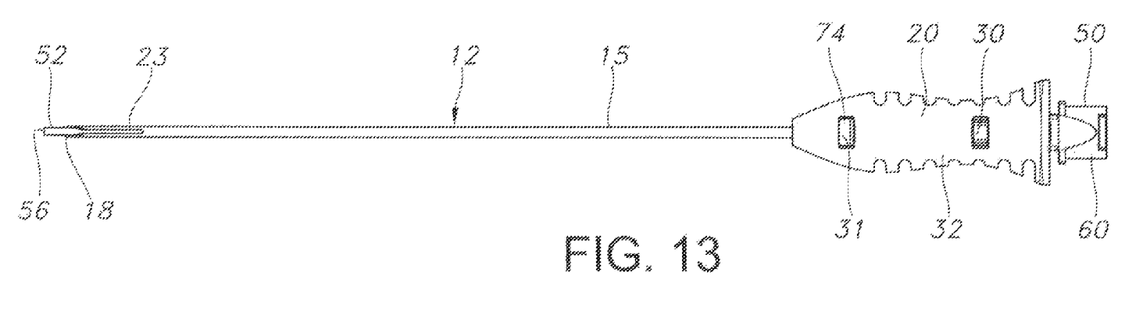
FIG. 13 is a top plan view of the safety needle assembly, but showing the stylus extending through the needle to render the assembly in a blunted position.
Figure 14:
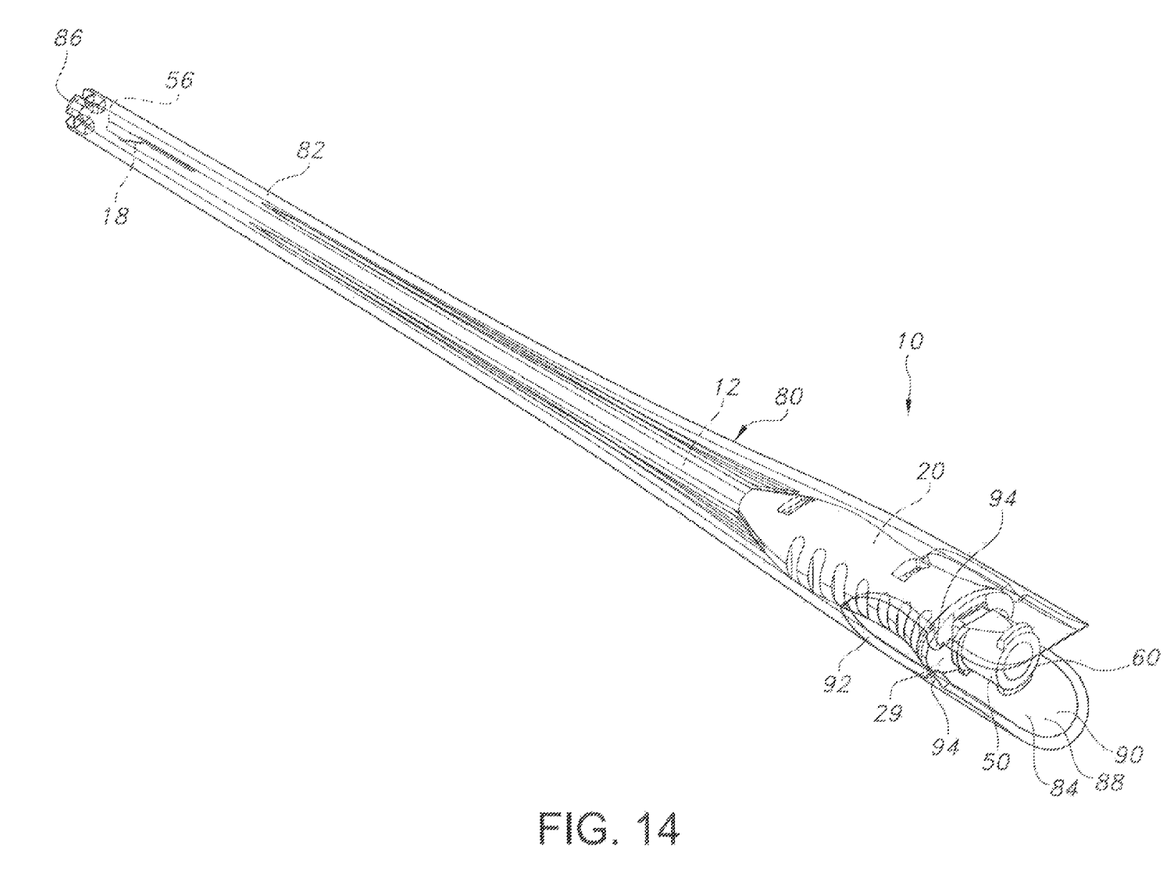
FIG. 14 is a perspective view of the needle assembly of FIG. 13, but shown positioned in the sheath.

A protective sheath 80, as shown in FIGS. 8, 10 and 14, may be provided, to isolate the sharp tip 17 of the distal end 18 of the needle 12 and protect the health care provider, until such time as the safety needle assembly 10 is removed from the sheath 80 for use. The sheath 80 is sized to hold the needle 12 with the stylus 50 positioned therewith. The sheath 80 has an outer surface 82 and an inner surface 84, and is shaped generally like a funnel having a closed end. The blunted safety needle assembly 10 is desirably positioned in the sheath 80, with the sharp tip 17 of the distal end 18 of the needle 12 positioned adjacent a closed end 86 of the sheath 80, and the needle hub 20 and stylus hub 50 accessible through an opening 88 in an open end 90 of the sheath 80. Slots 92 are positioned adjacent the opening 88 in an opposing, spaced-apart position. Each slot 92 is flanked by a pair of protuberances 94 formed along an edge 96 forming each slot. When a needle assembly 10 is positioned in the sheath 80, the edges 29 of the needle hub 20 are desirably positioned in the slots 92 and beneath the protuberances 94. The protuberances 94 catch the edges 29 of the hub 20, thereby preventing the needle hub 20 from falling out of the sheath 80. In this manner, the needle assembly 10 is releasably held in the sheath 80 until a health care provider removes the needle assembly 10 from the sheath 80. Once the needle assembly 10 has been used, it may be stored in the sheath 80 (FIG. 14). It will be appreciated that the sheath 80 is formed from a material having resilient qualities, which permits the sheath to operate as shown and/or described herein.

In a method of use of the blunted safety needle assembly, as illustrated in FIGS. 8-16, the stylus 50 is inserted into the hollow needle 12 by introducing the blunted distal end 56 of the stylus 50 into the opening 28 at the proximal end 40 of the needle hub 20. The shaft 52 of the stylus 50 is positioned through the opening 28 of the needle hub 20 and through the opening 14 of the shaft 15 of the needle, such that the outer surface 54 of the stylus contacts the inner surface 16 of the needle 12 and a portion of the outer surface 54 of the stylus hub 60 contacts the inner surface 38 of the needle hub 20.

The stylus hub 60 is desirably aligned with the needle hub 20 during this process, so that the retainer, that is, the flanges 68 of the stylus hub 50 and the clips 74 thereon are oriented to align with and move into the upper apertures or upper recesses 30 in the needle hub 20, thereby holding the stylus 50 to the needle hub 20 and preventing the stylus 50 from falling out of the needle 12 and/or hub 20. In such an orientation, the rim or ridge 63 on the outer circumference of the upper hub 62 contacts the wedges 47 on the shaft 44 of the handle 42. The wedges 47 act as stops, to prevent the movement of the stylus hub 60 and stylus 50 toward the distal end 18 of the needle 12. Such action is necessary so that the stylus 50 is not inadvertently pushed to move into and through the needle 12, wherein the end 56 of the stylus moves through the distal tip 17 of the needle 12 to blunt the needle assembly 10. Therefore, the handle 42 and wedges 47 thereon cooperate to hold the safety needle assembly 10 in a stable but un-deployed, un-blunted position.

It will be appreciated that a substance, such as, for example only, a radio-opaque substance may be loaded into the shaft 15 of the needle 12 prior to, or after, the introduction of the stylus 50 therein. Further, in addition to, or instead of a substance, a medical device, such as, for example, but not by way of limitation, a fastener 95, such as a T-bar and suture (often referred to as a "T-bar" fastener) often used for a gastropexy procedure, may be positioned in the shaft 15 of the needle 12 prior to, or after, the introduction of the stylus 50 therein. In this circumstance, the T-bar fastener 95 is introduced into the metal shaft 15 of the needle 12 via its distal end 18. The "bar" portion of the T-bar fastener 95 is moved upward into the shaft 15, so that it does not extend beyond the opening 14 of the needle 12. A suture 96 coupled to the T-bar fastener desirably extends through the slot 23 in the distal tip 17 and end 16 of the needle 12. The suture 96 may extend proximally, toward the needle hub 20 and may be releasably held by the hub 20 by passing the suture 96 through a "C"-clip 49 (not shown) on the hub 20. The suture 96 desirably, but not by way of limitation, includes a suture holder at an opposite end thereof (not shown).

The needle assembly 10 is desirably removed from the sheath 80, and a health care provider may introduce the needle 12 of the assembly 10 through a patient's skin and abdominal wall into a patient's stomach (not shown). The stylus 50, after the safety needle assembly 10 has been inserted into a target hollow organ or blood vessel, desirably acts to position a substance and/or a device, such as the T-bar fastener 95 and suture 96, in the patient.

Once the needle 12 has been moved to a desired depth so that, for example only, in a gastropexy procedure, the distal end 18 of the needle is positioned in a patient's stomach, and the stylus 50 is desirably activated by a health care provider. The provider moves the handle 42 and wedges 47 away from the needle hub 20 by pushing the handle portion 46 downward, thereby positioning the handle 42 in a transverse orientation relative to the needle assembly 10. The handle 42 may desirably, but not by way of limitation, be snapped off and removed from the needle hub 20. The stylus hub 60 is then pushed so that it moves toward the distal end 18 of the needle 12. This action pushes the blunt distal end 56 of the stylus 50 through the shaft 15 of the needle 12 such that the blunt distal end 56 of the stylus 50 contacts the fastener 95 in the shaft 15 and pushes or moves it out of the shaft 15 and out of the distal end 18 of the needle 12, thereby deploying it in a patient's stomach. It will be appreciated that a substance contained within the shaft 15 of the needle 12 is similarly moved out of the shaft 15 and disposed out of the needle 12 (not shown).

Moving the stylus 50 within the needle 12 not only moves one or more devices or substances out of the needle 12, but it also acts to position the needle assembly 10 in a blunted position. The blunted distal end 56 of the stylus 50 extends a distance beyond the sharp tip 17 at the distal end 18 of the needle 12, when the upper hub 62 of the stylus 50 is moved downward in the needle.

As the stylus 50 is moved toward the distal end 18 of the needle 12, the retainer, namely, the clips 76 on the flanges 68, move out of the upper apertures or upper recesses 30 in the needle hub 20 and continue in a movement toward the distal end of the needle hub 20 such that the clips 74 move into the lower apertures or lower recesses 31 of the needle hub 20. In this position, the retainer via the clips 74 act to lock the stylus 50 into a non-releaseable locked position relative to the needle 12. Therefore, the safety needle assembly 10 is placed in a stable, blunted position which cannot be altered; the clips 74 cannot be removed from the lower apertures 31 once they are positioned in them. In this blunted position, the safety needle assembly 10 is positioned in a permanently blunted position, and the safety needle assembly 10 is not useable again, and must be disposed of.

The needle 12 is desirably constructed from stainless steel, and may be an 18 gauge thin wall needle. The needle hub 20 is desirably constructed from plastic, and more desirably is a medical grade polycarbonate, medical grade macrolon, or the like. The needle tip may desirably be a non-coring needle tip, and may have a double bevel with reverse grind at the tip. The stylus 50 is desirably also constructed from stainless steel, and may be a 20 gauge thin wall hypodermic tube having a blunted, smooth distal end. The stylus hub 60 is desirably constructed from plastic, and more desirably is a medical grade polycarbonate, medical grade macrolon, or the like. It will be understood, however, that that any portion of the safety needle assembly 10, including the sheath 80, may be constructed from any material or combination of materials, in any gauge or thickness, with any variations, so long as the safety needle assembly 10 operates as shown and/or described herein.

While the present invention has been described in connection with certain preferred embodiments, it is to be understood that the subject matter encompassed by way of the present invention is not to be limited to those specific embodiments. On the contrary, it will be appreciated that some elements and/or articles may be used with other elements or articles. It is intended for the subject matter of the invention to include all alternatives, modifications and equivalents as can be included within the spirit and scope of the invention.

What is claimed is:

1. A hollow safety needle assembly used in the percutaneous fixation of a hollow organ, the assembly comprising:
   a needle including:
      a needle shaft having a sharp open distal end and an open proximal end, wherein a slot is formed at an edge of the sharp open distal end, and
      a needle hub at the proximal end of the needle shaft, the needle hub having an opening therethrough which is continuous with an opening provided through the shaft of the needle, the needle hub further comprising a handle at the proximal end thereof, the handle comprising a handle shaft axially aligned with the needle hub, a handle portion extending at an angle transversely away from the handle shaft, and a pair of opposing wedges positioned in a spaced-apart relationship on at least one of the handle shaft or the handle portion in an opposite direction of the handle portion; and
   a stylus including:
      a stylus shaft having a blunt distal end and a proximal end, and
      a stylus hub at the proximal end of the stylus shaft, the stylus hub having a proximal end and a distal end, the distal end of the stylus hub comprising at least one retainer constructed of a pair of flanges comprising free ends which taper outward and extend away from the stylus hub, the free ends defining a distal-most edge of the stylus hub and extending toward the blunt distal end of the stylus shaft, wherein when the stylus shaft is positioned inside of the needle shaft, the blunt distal end of the stylus shaft extends a distance toward the open distal end of the needle shaft, and when the stylus hub is positioned inside the needle hub, the stylus hub is configured to move between a first position defined by the free ends of the flanges being secured within a first pair of opposing recesses on an inner surface of the needle hub and a second, distal position defined by the free ends of the flanges being secured within a second, distal pair of opposing recesses on the inner surface of the needle hub such that, when in the second position, the blunt distal end of the stylus shaft extends through and beyond the sharp open distal end of the needle shaft,
      wherein the stylus shaft is held in the first position when the free ends of the flanges of the retainer extend outwardly into the first pair of recesses of the needle hub, and wherein the stylus shaft is held in the second, distal position when the free ends of flanges of the retainer extend outwardly into the second pair of recesses of the needle hub, the second position placing the assembly in a stable, blunted position, thereby locking the needle and stylus together in a fixed position and rendering the safety needle assembly in a safely blunted position which is visually verifiable by a user because the flanges are visible in the first and second opposing recesses when extending therethrough, and wherein the opposing wedges engage the stylus hub to prevent movement of the stylus hub and the stylus toward the distal end of the needle.

2. The safety needle assembly of claim 1, wherein the flanges flare slightly away from the stylus shaft.

3. The safety needle assembly of claim 2, where each of the flanges comprise one or clips extending outwardly from an outer surface thereof at each free end of the flanges.

4. The safety needle assembly of claim 1, where the clips comprise a generally triangular shape.

5. The safety needle assembly claim 1, wherein the handle is moveable to move the opposing wedges away from the stylus hub so that the stylus is moveable toward the distal end of the needle shaft.

6. The safety needle assembly of claim 1, wherein the handle is configured to break away from the needle hub.

7. The safety needle assembly of claim 1, wherein the handle shaft is integral with the proximal end of the needle hub.

8. The safety needle assembly of claim 1, wherein the handle portion extends substantially perpendicular with the handle shaft.

9. The safety needle assembly of claim 1, wherein the stylus further comprises a stylus edge at a proximal end of the stylus hub, the stylus edge comprising a protruding rim or ridge.

10. The safety needle assembly of claim 1, wherein the needle shaft is configured to hold an object in the distal end of the needle.

11. A hollow safety needle assembly used in the percutaneous fixation of a hollow organ, the assembly comprising:
a needle including:
  a needle shaft having a sharp open distal end and an open proximal end wherein a slot is formed at an edge of the sharp open distal end, and
  a needle hub at the proximal end of the needle shaft, the needle hub having an opening therethrough which is continuous with an opening provided through the shaft of the needle, the needle hub including at least a first recess and a second recess configured on an inner surface thereof; and
a handle comprising a handle shaft generally axially aligned with the needle hub, a handle portion extending at an angle transversely away from the handle shaft, and a moveable stop positioned on at least one of the handle shaft or the handle portion in an opposite direction of the handle portion, the moveable stop configured to engage the stylus hub to prevent movement of the stylus hub and the stylus toward the distal end of the needle, the handle shaft configured to move the moveable stop away from a stylus hub such that the stylus is moveable toward the distal end of the needle shaft, and wherein the moveable stop comprises a pair of wedges positioned in a spaced-apart relationship on at least one of the handle shaft or the handle portion; and a stylus including:
a stylus shaft having a blunt distal end and a proximal end, and a stylus hub at the proximal end of the stylus shaft, the stylus hub comprising a distal end and proximal end, the distal end including at least one retainer constructed of a pair of flanges comprising free ends which taper outward and extend a distance away from the stylus shaft, the free ends defining a distal-most edge of the stylus hub and extending toward the blunt distal end of the stylus shaft, the stylus hub further comprising a stylus edge at the proximal end, the stylus edge comprising a protruding rim or ridge;

wherein the safety needle assembly is configured to move from a first position in which:

the stylus hub is positioned inside the needle hub such that the blunt distal end of the stylus shaft extends a distance toward the open distal end of the needle shaft but is retained within the needle shaft by the free ends of the flanges extending outwardly and being secured within the first recess in the needle hub, and the moveable stop is positioned against the stylus edge at the proximal end of the stylus hub and the retainer is positioned such that at least a portion of the retainer exerts a transverse pressure on an inner surface of the needle hub causing resistance to axial movement of the stylus shaft and the free ends of the flanges do not contact the stylus shaft when positioned in the needle hub, to a second, distal position in which:

the moveable stop is moved away from the stylus edge at the proximal end of the stylus hub such that the blunt distal end of the stylus is moved in a distal direction to extend through and beyond the sharp open distal end of the needle shaft, and the blunt distal end is retained in its position when the free ends of the flanges of the stylus hub is moved to extend outwardly into the second recess in the needle hub placing the assembly in a stable, blunted fixed position, thereby locking the needle and stylus together which is visually verifiable by a user because the portion of the retainer is visible in the first and second recess when the portion of the retainer is positioned in the first or second recess of the needle hub.

12. The safety needle assembly of claim 11, wherein the handle is configured to break away from the needle hub.

13. The safety needle assembly of claim 11, wherein the handle shaft is integral with the proximal end of the needle hub.

14. The safety needle assembly of claim 11, wherein the handle portion extends substantially perpendicular with the handle shaft.

* * * * *